United States Patent
Sakaguchi et al.

(10) Patent No.: US 10,316,340 B2
(45) Date of Patent: Jun. 11, 2019

(54) GLUCOSE PRODUCTION METHOD AND GLUCOSE PRODUCED BY SAID METHOD

(71) Applicants: ACTEIIVE CORPORATION, Noda-shi, Chiba (JP); Masahiko Abe, Noda-shi (JP); Kengo Sakaguchi, Tsukuba-shi (JP); Shigeru Kido, Fukushima (JP)

(72) Inventors: Kengo Sakaguchi, Tsukuba (JP); Yoshihiro Kanai, Takasaki (JP); Tatsushi Ruike, Sannohe-gun (JP)

(73) Assignees: ACTEIIVE CORPORATION, Noda-Shi (JP); Masahiko Abe, Noda-Shi (JP); Kengo Sakagchi, Tsukuba-Shi (JP); Shigeru Kido, Ishikawa-Gun (JP)

( * ) Notice: Subject to any disclaimer, the term of this patent is extended or adjusted under 35 U.S.C. 154(b) by 118 days.

(21) Appl. No.: 14/894,329

(22) PCT Filed: Jun. 2, 2014

(86) PCT No.: PCT/JP2014/064587
§ 371 (c)(1),
(2) Date: Nov. 25, 2015

(87) PCT Pub. No.: WO2014/192958
PCT Pub. Date: Dec. 4, 2014

(65) Prior Publication Data
US 2016/0108446 A1    Apr. 21, 2016

(30) Foreign Application Priority Data

May 31, 2013  (JP) ................. 2013-115236

(51) Int. Cl.
*C12P 19/02* (2006.01)
*C12P 19/14* (2006.01)
*C13K 1/02* (2006.01)

(52) U.S. Cl.
CPC ............... *C12P 19/02* (2013.01); *C12P 19/14* (2013.01); *C13K 1/02* (2013.01)

(58) Field of Classification Search
None
See application file for complete search history.

(56) References Cited

U.S. PATENT DOCUMENTS

| 8,785,154 B2 | 7/2014 | Boy et al. |
| 2008/0213850 A1* | 9/2008 | Shimoda ................... C12P 7/08 435/165 |

FOREIGN PATENT DOCUMENTS

| JP | 2006230365 A | 9/2006 |
| JP | 200835853 A | 2/2008 |
| JP | 201156456 A | 3/2011 |
| JP | 2011519550 A | 7/2011 |
| JP | 2012527243 A | 11/2012 |
| WO | 2010135365 A2 | 11/2010 |
| WO | 2012163668 A1 | 12/2012 |

OTHER PUBLICATIONS

Cai et al. "Production and Distribution of Endoglucanase, Cellobiohydrolase, and b-Glucosidase Components of the Cellulolytic System of Volvariella volvacea, the Edible Straw Mushroom" Applied and Environmental Microbiology, Feb. 1999, p. 553-559.*
Chundawat et al. "Proteomics-based Compositional Analysis of Complex Cellulase-Hemicellulase Mixtures" J. Proteome Res. 2011, 10, 4365-4372.*
Maleki et al. "Characterization of Cellulose Synthesis in Plant Cells" The Scientific World Journal vol. 2016, Article ID 8641373, 8 pages.*
Philippidis et al. "Study of the Enzymatic Hydrolysis of Cellulose for Production of Fuel Ethanol by the Simultaneous Saccharification and Fermentation Process" Biotechnology and Bioengineering, vol. 41, pp. 846-853 (1993).*
Worthington Biochemical Corporation "Cellulase" accessed at http://www.worthington-biochem.com/cel/default.html on Mar. 28, 2018, 3pgs.*
Wang "Experiment No. 4:Cellulose Degradation" available online May 23, 2009 at http://www.eng.umd.edu:80/~nsw/ench485/lab4.htm 6 pgs.*
International Search Report (ISR) dated Aug. 5, 2014, issued for International application No. PCT/JP2014/064587. (2 pages).

\* cited by examiner

*Primary Examiner* — Thane Underdahl
(74) *Attorney, Agent, or Firm* — Law Office of Katsuiro Arai

(57) ABSTRACT

A glucose production method is characterized in that glucose is produced from organisms that hold at least a disaccharide inside the body, which organisms utilize a cellulose source as food or for nutrients, particularly insects, crustaceans, and mushrooms.

2 Claims, 1 Drawing Sheet

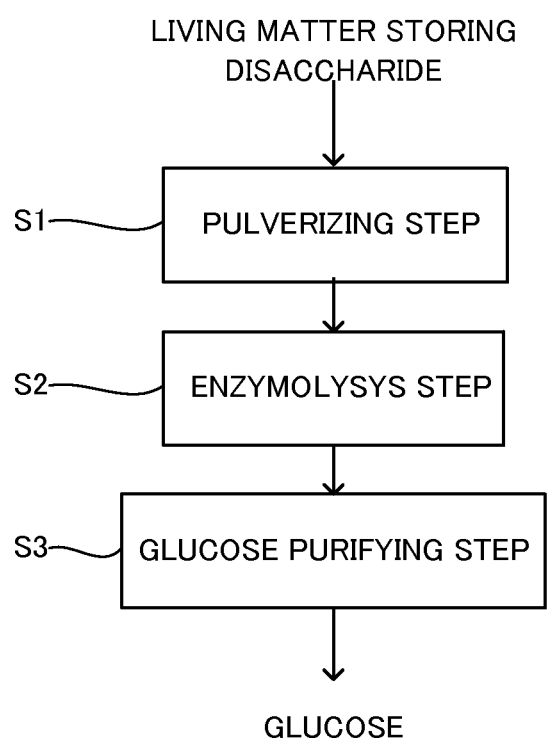

GLUCOSE PRODUCTION METHOD AND GLUCOSE PRODUCED BY SAID METHOD

This application is the U.S. National Phase under 35 U.S.C. § 371 of International Application PCT/JP2014/064587, filed Jun. 2, 2014, which claims priority to Japanese Patent Application No. 2013-115236, filed May 31, 2013. The International Application was published under PCT Article 21(2) in a language other than English.

TECHNICAL FIELD

The present invention relates to a glucose production method that uses living matter that holds at least a disaccharide inside the body as a raw material, and glucose produced by this method.

BACKGROUND ART

In recent years, there has been an increase in the use of glucose in industrial applications as a starting material for bioethanol and polymeric materials that serve as alternative fuels for petroleum fuel.

Conventionally, as described in Patent Literature 1, glucose for industrial use has been produced from potatoes, grains such as corn, wheat, barley, rye, triticale, and rice, or plants used as raw material for sugar such as sugarcane and sugar beets. However, there is concern that, as industrial application accelerates, the transaction prices of grains and plants used as raw material for sugar that are traded for use as food will rise, thereby cutting into household budgets and playing a part in famine in developing countries. Therefore, attempts are being made to obtain glucose through saccharification of a cellulose raw material.

Patent Literature 1: Japanese Patent Laid-open Publication No. 2011-915550

DISCLOSURE OF INVENTION

Problem to be Solved by the Invention

However, cellulose raw materials have very rigid crystalline components. Therefore, numerous steps are required to obtain glucose, such as pretreatment by immersion in an alkaline solution or the like before enzymolysis, and a solubilization treatment using a strong acid or the like.

It is known that, in nature, there exists living matter that consumes such cellulose sources as food and holds, inside the body, sugar obtained through decomposition of the cellulose inside the body Therefore, an object of the present invention is to provide a glucose production method for producing glucose from living matter that uses such cellulose sources as food or for nutrients, particularly insects, crustacean, and mushrooms that can be found in large populations in nature, and glucose produced by this method.

Means for Solving Problem

To achieve the above-described object, a first aspect of the glucose production method of the present invention is characterized in that glucose is produced from living matter that holds at least a disaccharide inside the body. A second aspect is characterized in that the disaccharide is trehalose and/or cellobiose. A third aspect is characterized in that glucose is produced by performing enzymolysis on the living matter. A fourth aspect is characterized in that glucose is produced by enzymolysis being performed on at least the disaccharide in the living matter. A fifth aspect is characterized in that glucose is produced by performing enzymolysis using trehalase when the disaccharide is trehalose and by performing enzymolysis using β-glucosidase when the disaccharide is cellobiose. A sixth aspect is characterized in that the living matter is an insect, crustacean, or a mushroom.

According to the first to sixth aspects of the glucose production method of the present invention, such as those described above, glucose, which is a monosaccharide, can be easily produced by enzymolysis being performed on living matter that holds a disaccharide inside the body, particularly insects, crustacean, and mushrooms.

The glucose of the present invention is characterized by being produced using a production method according to any of the first to sixth aspects.

The glucose of the present invention such as this can be provided on the market at a low price because insects, crustacean, or mushroom, which can be found in very large populations in nature, are used as the raw material.

Effect of the Invention

In the glucose production method of the present invention, glucose, which is a monosaccharide, can be easily produced by enzymolysis being performed on living matter that holds a disaccharide inside the body.

In addition, the glucose of the present invention can be provided on the market at a low price through effective use of, for example, locusts and migratory locusts, which cause locust plagues, the chrysalides of silkmoths, which are discarded in large amounts during silk cultivation, and mushrooms and crustacean such as water fleas and *Artemia*, which can be easily propagated.

BRIEF DESCRIPTION OF DRAWINGS

FIG. 1 is a flowchart of production steps in a glucose production method according to an embodiment of the present invention.

EXPLANATIONS OF LETTERS OR NUMERALS

| | |
|---|---|
| S1 | pulverizing step |
| S2 | enzymolysis step |
| S3 | glucose purifying step |

BEST MODE(S) FOR CARRYING OUT THE INVENTION

A specific embodiment of a glucose production method of the present invention will hereinafter be described in detail with reference to FIG. 1.

The glucose production method of the present invention is a method for producing glucose mainly from living matter that holds a disaccharide inside the body.

Living matter that holds a disaccharide inside the body include insects, crustacean, and mushrooms.

More specifically, insects include, for example, caelifera, such as locusts, Asiatic locusts, Chinese grasshoppers (*Acrida cinerea*), and *Atractomorpha lata*; isoptera, such as *reticulitermes speratus* and *coptptermes formosanus*; phasmida, such as *Pylaemenes guangxiensis* and *Entoria japonica*; hymenoptera such as Japanese honey bees (*Apis*

*cerana japonica*), Western honey bees (*Apis mellifera*), and wasps (vespinae); and lepidoptera such as silkmoths (*Bombyx mori*), *pieris rapae*, and swallowtail butterflies.

Crustacean includes, for example, shrimp, crabs, krill, barnacles, water fleas, and *Artemia*.

Mushrooms include, for example, shiitake, shimeji, maitake (*Grifola frondosa*), nameko (*Pholiota nameko*), *Auricularia auricular-judae*, and *Pleurotus eryngii*.

Insects and crustaceans store trehalose inside the body as blood sugar. Therefore, glucose can be easily produced by performing enzymolysis on the insect or crustacean using a trehalase that performs enzymolysis on trehalose as a substrate. In addition to trehalose, the disaccharide held inside the body may be cellobiose that is produced when cellulose, which is food, is being decomposed.

Inside the body of living matter that uses cellulose as food, such as insects, highly soluble cello-oligosaccharide, such as cellotriose and cellotetraose, may be held, in addition to the disaccharide. The cello-oligosaccharide can also be enzymatically decomposed into glucose.

The glucose production method of the present invention is designed such that glucose is produced by performing enzymolysis on living matter that holds disaccharide inside the body, and thereby enzymatically decomposing at least the disaccharide held inside the body.

In addition, the enzyme used in enzymolysis can be selected as appropriate based on the type of disaccharide held in the living matter. As shown in Table 1, for example, when the living matter holds trehalose, trehalase can be used. When the living matter holds cellobiose, β-glucosidase can be used. Furthermore, when the living matter holds cello-oligosaccharide, β-glucosidase, endoglucanase, cellobiohydrolase, or the like can be additionally used. In addition, the enzyme may be a commercially available enzyme, or an enzyme derived from bacteria, plants, or animals. In particular, insects and crustacean that holds disaccharide often also hold an enzyme for enzymatically decomposing disaccharide and cello-oligosaccharide, together with the disaccharide and cello-oligosaccharide. Therefore, the insect or crustacean itself used as the raw material or a cellulolytic enzyme extracted from the insect or crustacean used as the raw material may be used.

TABLE 1

| Substrate | Enzyme |
| --- | --- |
| Trehalose | Trehalase |
| Cellobiose | β-glucosidase, endoglucanase |
| Cellotriose | β-glucosidase, endoglucanase, cellobiohydrolase |
| Cellotetraose | β-glucosidase, endoglucanase, cellobiohydrolase |

More specifically, as shown in FIG. 1, the glucose production method of the present invention is that in which glucose is produced by performing a pulverizing step S1 of pulverizing living matter that holds a disaccharide inside the body with a mixer or the like. Thereafter, an enzymolysis step S2 of mixing the pulverized matter with a decomposing enzyme that decomposes the disaccharide and performing glycolysis is performed to produce glucose. A glucose purifying step S3 of extracting the produced glucose is also performed.

The pulverizing step S1 can be omitted depending on the form and state of the insect used as the raw material. For example, when the insect serving as the raw material is extremely small and does not require pulverization, the pulverizing step S1 can be omitted and the enzymolysis step S2 can be immediately performed.

In the glucose production method of the present invention, glucose, which is a monosaccharide, can be easily produced by living matter that holds a disaccharide inside the body being decomposed to sugar by a decomposing enzyme. In addition, because insects that exist in large numbers in nature are used as the raw material, the glucose produced by the glucose production method of the present invention can be provided on the market at a low price through effective use of locusts and migratory locusts, which cause locust plagues, the chrysalides of silkmoths, which are discarded in large amounts during silk cultivation, and mushrooms and crustacean such as water fleas and *Artemia*, which can be easily propagated.

Examples of the glucose production method of the present invention will be described below.

Example 1

In example 1, using 10 g of commercially available dried locusts as the insect serving as the raw material, 10 g of locust power was obtained by pulverizing the dried locusts in a mortar. Next, the mortar was washed with 10 mL of 50 mM sodium phosphate buffer solution over ten washings, and the 10 g of locust powder was suspended. A 100 mg/mL substrate suspension was thereby obtained. 40 μL of the 100 mg/mL substrate suspension was placed in a 1.5 mL microtube. 10 μL of trehalase (T8778, manufactured by Sigma-Aldrich Corporation) and 10 μL of a cellulase suspension, in which 500 μg of cellulase derived from *Trichoderma viride* are suspended per 1 mL of a 20 mM sodium acetate buffer solution, were added. Incubation was performed for 24 hours at 37° C. As a result of quantification being performed on the produced glucose using a glucose quantification reagent (LabAssay (registered trademark) Glucose, manufactured by WAKO Pure Chemical Industries, Ltd.), 79.2 mg/g (glucose weight/substrate weight) of glucose was obtained.

Example 2

In example 2, using 5 g of commercially available brine shrimp (genus *Artemia*) diapause eggs as the crustacean serving as the raw material, 5 g of brine shrimp diapause egg paste were obtained by pulverizing the brine shrimp diapause eggs in a mortar. Next, the mortar was washed with 10 mL of 50 mM sodium phosphate buffer solution over five washings, and the 5 g of brine shrimp diapause egg powder was suspended. A 100 mg/mL substrate suspension was thereby obtained. 40 μL of the 100 mg/mL substrate suspension was placed in a 1.5 mL microtube. 10 μL of trehalase (T8778, manufactured by Sigma-Aldrich Corporation) was added. Incubation was performed for 24 hours at 37° C. As a result of quantification being performed on the produced glucose using a glucose quantification reagent (LabAssay (registered trademark) Glucose, manufactured by WAKO Pure Chemical Industries, Ltd.), 113.4 mg/g (glucose weight/substrate weight) of glucose was obtained.

Example 3

In example 3, 10 g of commercially available *Pleurotus eryngii* was used as the mushroom serving as the raw material. The *Pleurotus eryngii* was cut into 0.5 cm squares and pulverized with a mixer with 30 mL of a 50 mM sodium phosphate buffer solution added thereto. Then, the interior of the mixer was washed with 10 mL of the 50 mM sodium phosphate buffer solution over seven washings, and the 10 g of *Pleurotus eryngii* was suspended. A 100 mg/mL substrate suspension was thereby obtained. 40 µL of the 100 mg/mL substrate suspension was placed in a 1.5 mL microtube. 10 µL of trehalase (T8778, manufactured by Sigma-Aldrich Corporation) was added. Incubation was performed for 24 hours at 37° C. As a result of quantification being performed on the produced glucose using a glucose quantification reagent (LabAssay (registered trademark) Glucose, manufactured by WAKO Pure Chemical Industries, Ltd.), 133.7 mg/g (glucose weight/substrate weight) of glucose was obtained.

It is clear from example 1 to example 3, described above, that as a result of the glucose production method of the present invention being used, glucose, which is a monosaccharide, can be easily produced from living matter that holds a disaccharide inside the body, that is, the locusts, brine shrimp, and *Pleurotus eryngii* in the present examples. As a result of glucose being produced in this way from living matter that holds a disaccharide inside the body, low-priced glucose can be provided on the market because insects, crustacean, and mushrooms, which can be found in large populations in nature, are used as the raw material.

The invention claimed is:

1. A glucose production method comprising performing:
   a) enzymolysis using trehalase and cellulase on a dried insect body that stores trehalose and cellobiose as a disaccharide, thereby enzymatically decomposing the disaccharide to produce glucose and
   b) isolating the glucose from the enzymolysis mixture produced in a).

2. The glucose production method according to claim 1, wherein the dried insect body is a dried body of locusts.

* * * * *